United States Patent
Elsesser et al.

(10) Patent No.: US 8,360,995 B2
(45) Date of Patent: Jan. 29, 2013

(54) WIRE GUIDE

(75) Inventors: James C. Elsesser, Bloomington, IN (US); Christopher L. Hruska, Indianapolis, IN (US); Aaron Weeks, Bloomington, IN (US); Jason C. Urbanski, Ellettsville, IN (US); James M. Carlson, Bloomington, IN (US); Richard W. Ducharme, Winston-Salem, NC (US); Alex Etwil, Copenhagen (DK)

(73) Assignee: Cook Medical Technologies LLC, Bloomington, IN (US)

( * ) Notice: Subject to any disclaimer, the term of this patent is extended or adjusted under 35 U.S.C. 154(b) by 9 days.

(21) Appl. No.: 12/677,973

(22) PCT Filed: Sep. 15, 2008

(86) PCT No.: PCT/US2008/076396
§ 371 (c)(1),
(2), (4) Date: May 17, 2010

(87) PCT Pub. No.: WO2009/039063
PCT Pub. Date: Mar. 26, 2009

(65) Prior Publication Data
US 2010/0249654 A1 Sep. 30, 2010

Related U.S. Application Data

(60) Provisional application No. 60/973,322, filed on Sep. 18, 2007.

(51) Int. Cl.
*A61M 25/00* (2006.01)
*B21D 39/03* (2006.01)
*B23P 11/00* (2006.01)
*B23P 17/04* (2006.01)

(52) U.S. Cl. .............. 600/585; 29/428; 29/592

(58) Field of Classification Search .............. 600/433, 600/434, 585; 604/164.13; 29/592, 896.1, 29/428
See application file for complete search history.

(56) References Cited

U.S. PATENT DOCUMENTS 5,234,003 A    8/1993  Hall
5,238,004 A    8/1993  Sahatjian et al.
(Continued)

FOREIGN PATENT DOCUMENTS

CH    674943 A5 *  8/1990
DE    19823414      6/1999
(Continued)

OTHER PUBLICATIONS

International Search Report and Written Opinion for PCT/US2008/076396 dated Feb. 4, 2009 (18 pgs).
(Continued)

*Primary Examiner* — Max Hindenburg
*Assistant Examiner* — Jonathan M Foreman
(74) *Attorney, Agent, or Firm* — Brinks Hofer Gilson & Lione

(57) ABSTRACT

The present invention provides a wire guide (20) suitable for use in a body vessel, such as a peripheral vessel. The wire guide comprises a core member (22) and a first coiled member (40), each having proximal and distal ends. In one embodiment, the core member comprises at least one recessed portion (36), wherein the proximal end of the first coiled member is seated at least partially within the recessed portion to form a substantially flush exterior surface with the core member. The wire guide further preferably comprises a second coiled member (50) having proximal and distal ends, wherein the second coiled member is disposed distal to the first coiled member. The distal end of the first coiled member may be partially intertwined with the proximal end of the second coiled member. A shaping ribbon (60) may be disposed substantially beneath the second coiled member to achieve a desired curvature at the distal tip of the wire guide.

18 Claims, 2 Drawing Sheets

U.S. PATENT DOCUMENTS

| | | | |
|---|---|---|---|
| 5,377,690 | A | 1/1995 | Berthiaume |
| 5,480,382 | A | 1/1996 | Hammerslag et al. |
| 5,509,411 | A | 4/1996 | Littmann et al. |
| 5,609,629 | A | 3/1997 | Fearnot et al. |
| 5,637,089 | A | 6/1997 | Abrams et al. |
| 5,645,064 | A | 7/1997 | Littmann et al. |
| 5,682,885 | A | 11/1997 | Littmann et al. |
| 5,699,796 | A | 12/1997 | Littmann et al. |
| 5,711,298 | A | 1/1998 | Littmann et al. |
| 5,769,796 | A | 6/1998 | Palermo et al. |
| 5,876,356 | A | 3/1999 | Viera et al. |
| 5,902,272 | A | 5/1999 | Eggers et al. |
| 5,954,672 | A * | 9/1999 | Schwager ............... 600/585 |
| 5,957,842 | A | 9/1999 | Littmann et al. |
| 5,967,978 | A | 10/1999 | Littmann et al. |
| 6,021,355 | A | 2/2000 | Shchervinsky |
| 6,039,700 | A * | 3/2000 | Sauter ............... 600/585 |
| 6,141,576 | A | 10/2000 | Littmann et al. |
| 6,387,060 | B1 | 5/2002 | Jalisi |
| 6,488,637 | B1 | 12/2002 | Eder et al. |
| 6,491,648 | B1 | 12/2002 | Cornish et al. |
| 6,508,803 | B1 | 1/2003 | Horikawa et al. |
| 6,544,197 | B2 | 4/2003 | DeMello |
| 6,679,853 | B1 | 1/2004 | Jalisi |
| 6,740,050 | B2 | 5/2004 | D'Aquanni et al. |
| 6,830,638 | B2 | 12/2004 | Boylan et al. |
| 7,122,048 | B2 | 10/2006 | DiMatteo et al. |
| 2003/0216668 | A1 | 11/2003 | Howland et al. |
| 2004/0064069 | A1 | 4/2004 | Reynolds et al. |
| 2004/0123915 | A1 | 7/2004 | Jalisi |
| 2005/0027212 | A1 * | 2/2005 | Segner et al. ............... 600/585 |
| 2005/0273020 | A1 | 12/2005 | Whittaker et al. |
| 2008/0097247 | A1 * | 4/2008 | Eskuri ............... 600/585 |
| 2008/0161726 | A1 * | 7/2008 | Itou ............... 600/585 |
| 2008/0255518 | A1 * | 10/2008 | Albers et al. ............... 604/164.13 |

FOREIGN PATENT DOCUMENTS

| | | |
|---|---|---|
| EP | 0343509 | 11/1989 |
| EP | 0739641 | 10/1996 |
| EP | 1464358 | 10/2004 |
| EP | 1698370 | 9/2006 |
| EP | 1938859 | 7/2008 |
| WO | WO9816274 | 4/1998 |
| WO | WO9944668 | 9/1999 |
| WO | WO03010352 | 12/2003 |
| WO | WO2009039063 | 3/2009 |

OTHER PUBLICATIONS

International Preliminary Report on Patentability for PCT/US2008/076396 dated Mar. 24, 2010 (9 pgs.).

* cited by examiner

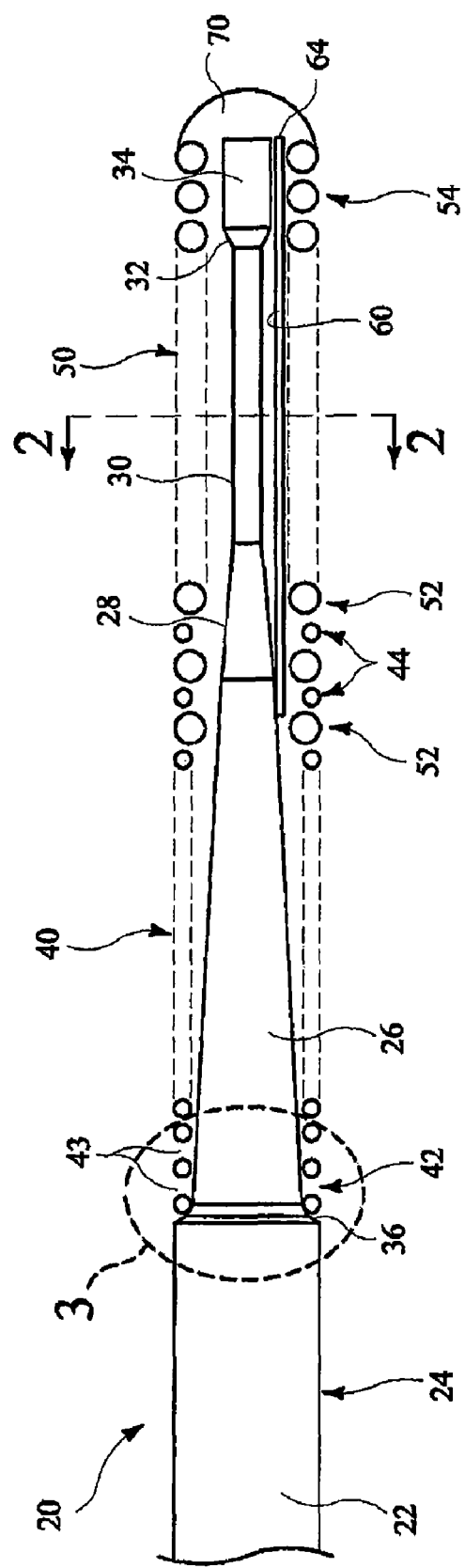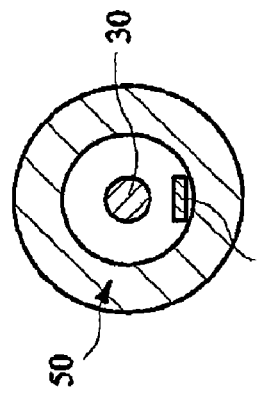
FIG. 1
FIG. 2

WIRE GUIDE

RELATED APPLICATIONS

The present patent document is a §371 filing based on PCT Application Serial No. PCT/US2008/076396, filed Sep. 15, 2008 (and published as WO 2009/039063 A1 on Mar. 26, 2009), designating the United States and published in English, which claims the benefit of the filing date under 35 U.S.C. §119(e) of Provisional U.S. Patent Application Ser. No. 60/973,322, filed Sep. 18, 2007. All of the foregoing applications are hereby incorporated by reference in their entirety.

PRIORITY CLAIM

This invention claims the benefit of priority of U.S. Provisional Application Ser. No. 60/973,322, entitled "Wire Guide," filed Sep. 18, 2007, the disclosure of which is hereby incorporated by reference in its entirety.

BACKGROUND

The present invention relates generally to apparatus and methods for treating vascular conditions, and more specifically, to a wire guide for use in a body vessel.

Wire guides are commonly used in vascular procedures, such as angioplasty procedures, diagnostic and interventional procedures, percutaneous access procedures, and radiological and neurological procedures. In general, wire guides may be used to introduce a wide variety of medical devices into the vascular system.

For example, wire guides may be employed to treat atherosclerosis and other occlusive diseases, which are prevalent among a significant portion of the population. In such diseases, atherosclerotic plaque forms on the walls of the vessel and blocks or restricts blood flow through the vessel. Atherosclerosis commonly affects the coronary arteries, the aorta, the iliofemoral arteries and the carotid arteries. Several serious conditions may result from the restricted blood flow, such as ischemic events.

Various procedures are known for treating stenoses in the arterial or peripheral vasculature, such as the use of balloon angioplasty and stenting. During a balloon angioplasty procedure, a catheter having a deflated balloon attached thereto is positioned across a constricting lesion, and the balloon is then inflated to widen the lumen to partially or fully restore patency to the vessel. Stenting involves the insertion of a usually tubular member into a vessel, and may be used alone or in conjunction with an angioplasty procedure. Stents may be self-expanding or balloon expandable. Self-expanding stents typically are delivered into a vessel within a delivery sheath, which constrains the stent prior to deployment. When the delivery sheath is retracted, the stent is allowed to radially expand to its predetermined shape. If the stent is balloon expandable, the stent typically is loaded onto a balloon of a catheter, inserted into a vessel, and the balloon is inflated to radially expand the stent.

Wire guides also may be used in peripheral or arterial vessels for purposes other than occlusion treatment and stent deployment, such as delivering devices for providing embolic protection and retrieving foreign bodies. Generally, during each of the foregoing procedures, a wire guide is first inserted into a patient's vessel, e.g., under fluoroscopic guidance. The wire guide then is advanced toward a target site in the patient's vasculature. For example, the distal end of the wire guide may be advanced through a stenosis. Then, various medical components, such as a balloon catheter and/or stent, may be distally advanced over the wire guide to the target site.

Commercially available wire guides may comprise flexible distal regions in an effort to facilitate navigation through the tortuous anatomy of a patient's vasculature. For example, wire guides may employ a coil disposed to overlay a reduced diameter portion of core wire near the distal end of the wire guide. The coil may be adhered to the core wire using techniques such as soldering. One drawback associated with existing devices is that the solder may form a bumpy or inconsistent surface between the coil and the core wire. Moreover, the provision of solder may increase the overall profile of the wire guide in the vicinity of its attachment to the coil.

Where such wire guides having flexible distal regions are used, it also may be difficult to insert a medical component over the wire guide, for example, because the flexible distal region may be susceptible to kinking. However, if the distal region of the wire guide is too rigid, then it may not be sufficiently flexible to navigate the tortuous anatomy.

In view of the foregoing, there is a need for a guide wire suitable for navigating tortuous anatomy, permitting advancement of medical components, and having a reduced diameter profile and substantially smooth outer surface.

SUMMARY

The present invention provides a wire guide suitable for use in a body vessel, such as a peripheral vessel. The wire guide comprises a core member and a first coiled member, each having proximal and distal ends.

In a first embodiment, the core member comprises at least one recessed portion, such as a curved portion, disposed between the proximal and distal ends of the core member. The proximal end of the first coiled member is seated at least partially within the curved portion to form a substantially flush exterior surface with the core member. At least one taper preferably is disposed distal to the curved portion of the core member, and the taper reduces the diameter of the core member at a location distal to the curved portion.

The proximal end of the first coiled member preferably comprises adjacent turns that are spaced apart further relative to other adjacent turns of the first coiled member. The further spaced apart turns permit solder to be disposed between the first coiled member and the core member. The solder is disposed substantially between the further spaced apart adjacent turns at the proximal end of the first coiled member, such that the solder does not significantly increase the overall profile of the wire guide.

In a preferred embodiment, the wire guide further comprises a second coiled member having proximal and distal ends, wherein the second coiled member is disposed distal to the first coiled member. The distal end of the first coiled member may be at least partially intertwined with the proximal end of the second coiled member. The first coiled member may comprise stainless steel and the second coiled member may comprise palladium, thereby providing enhanced visibility near the distal tip of the wire guide.

Preferably, the cross-sectional diameter of the wire that makes up the second coiled member is greater than the cross-sectional diameter of the wire that makes up the first coiled member. Since the outer diameter of the core member generally is smaller within the second coiled member, the greater cross-sectional profile of the second coiled member does not increase the overall outer diameter of the wire guide.

The wire guide also may comprise a shaping ribbon disposed adjacent to the distal end of the core member. The shaping ribbon may be disposed substantially beneath the second coiled member, and may comprise a stainless steel wire having a substantially rectangular cross-section. In use, the shaping ribbon may be bent prior to insertion of the wire guide, in order to achieve a desired curvature at the distal tip of the wire guide.

Various dimensions and materials associated with the core member, the first and second coiled members, and the shaping ribbon are provided. The dimensions and materials listed illustrate novel features and combinations of a wire guide, but are merely exemplary, and not intended to be limiting.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following figures and description. The components in the figures are not necessarily drawn to scale, emphasis instead being placed upon illustrating the principles of the invention. Moreover, in the figures, like referenced numerals designate corresponding parts throughout the different views.

FIG. 1 is side-sectional view of a wire guide in accordance with a first embodiment.

FIG. 2 is a cross-sectional view along line 2-2 of FIG. 1

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patient's anatomy during a medical procedure.

Figure 3:
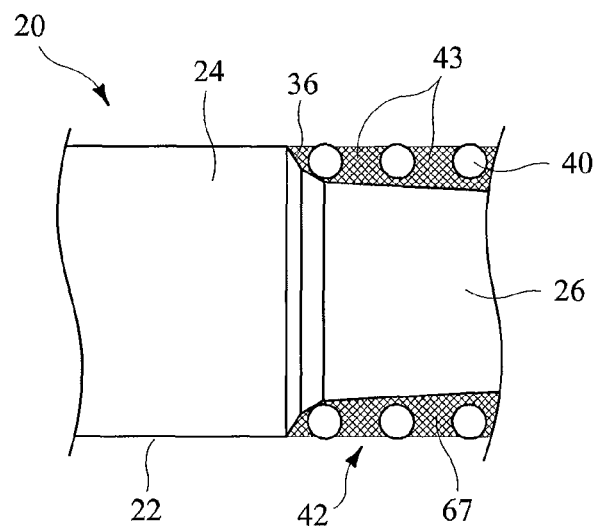
FIG. 3 is a side view illustrating features of the wire guide of FIG. 1.

Referring now to FIGS. 1-3, a first embodiment of a wire guide is shown. In FIG. 1, the wire guide 20 generally comprises a core member 22 having proximal and distal ends. The core member 22 comprises a main body 24 having a substantially cylindrical outer diameter. The main body 24 preferably spans from the proximal end of the core member 22 towards the distal end and terminates before the core member 22 transitions into one or more tapered sections, as explained further below. In a preferred embodiment, the outer diameter of the main body 24 ranges from about 0.013-0.014 inches.

The core member 22 may be manufactured from any suitable material for use in an interventional procedure. For example, the core member 22 may comprise stainless steel, a nickel-titanium alloy such as nitinol, or any other suitable material or alloy having a flexibility adapted to navigate a patient's vasculature and strength sufficient to deliver an interventional device to a desired anatomical site.

The core member 22 may include a nickel-titanium alloy, which may comprise a superelastic or linear elastic nickel-titanium alloy. As is known in the art, a superelastic nickel-titanium alloy may undergo a reversible phase transformation between a lower temperature phase (martensite) and a higher temperature phase (austenite) that allows it to "remember" and return to a previous configuration. Strain introduced in the alloy in the martensitic phase to achieve a shape change may be substantially recovered upon completion of a reverse phase transformation to austenite, allowing the alloy to return to the previous configuration. Superelastic alloys may recover up to 8-10% strain. It is also known that cold-worked martensitic nickel-titanium alloys (linear elastic nickel-titanium alloys) can provide a recoverable strain of several percent (e.g., 3-4%) when deformed without a phase transformation. Such linear elastic nickel-titanium alloys may exhibit substantially linear stress-strain behavior. The core member 22 preferably comprises a linear elastic nickel-titanium alloy.

The core member 22 further preferably comprises a first taper 26 disposed distal to the main body 24. The first taper 26 may span a length of approximately 2 inches and may reduce the diameter of the core member 22 from about 0.013 inches to about 0.0055 inches. A second, less gradual taper 28 optionally is disposed just distal to the first taper 26, as shown in FIG. 1. The second taper 28 may span a length of approximately 0.28 inches and may reduce the diameter of the core member 22 further from about 0.0055 inches to about 0.0030 inches. A reduced diameter section 30 of the core member 22, having an outer diameter of about 0.0030 inches, extends distally for about 0.72 inches towards the distal tip of the wire guide 20. If desired, an outward taper 32 may be provided, thereby providing a distal tip section 34 that may have a slightly increased outer diameter relative to the reduced diameter section 30, as shown in FIG. 1.

The dimensions and configurations listed above are particularly suitable for use in peripheral vessel interventions, although they may be used in other applications such as coronary procedures. Such dimensions are provided for reference purposes only and are not intended to be limiting.

Referring still to FIG. 1, the wire guide 20 further comprises a first coiled member 40 having a proximal end 42 and a distal end 44. The first coiled member 40 may be manufactured, for example, from a wound spring wire having a round or flat wire configuration. The first coiled member 40 may be attached to the core member 22 using any suitable technique, for example, soldering, brazing, welding or using a biocompatible glue. Preferably, the first coiled member 40 is attached to the core member 22 using a solder 67, as shown in FIG. 3 and explained in further detail below.

Figure 4:
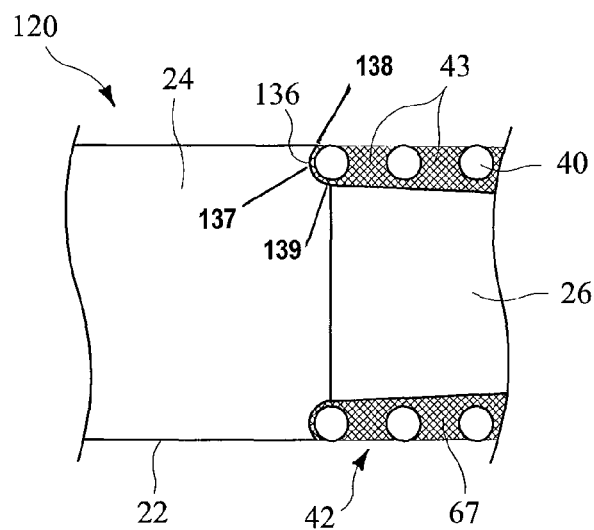
FIG. 4 is a side view illustrating an alternative embodiment of the wire guide of FIGS. 1-3.
Figure 5:
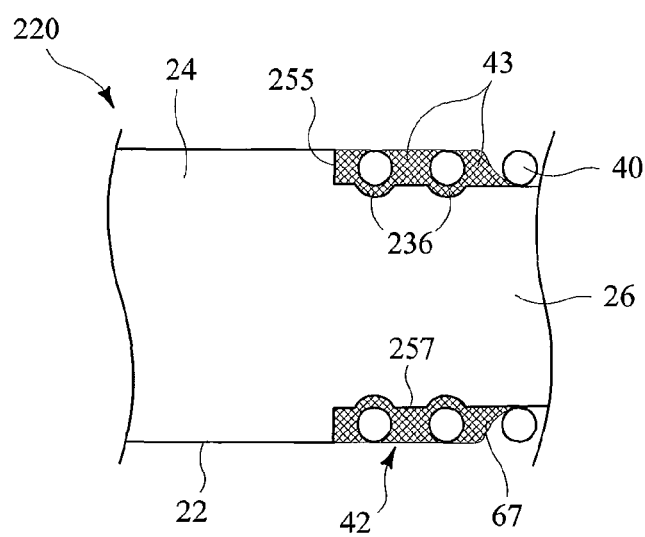
FIG. 5 is a side view illustrating a further alternative embodiment of the wire guide of FIGS. 1-3.

The core member 22 preferably comprises at least one recessed portion 36. The recessed portion 36 preferably comprises a curved portion 36, as described below. The curved portion 36 may be disposed between the main body 24 and the taper 26, as generally shown in FIG. 1 and FIG. 3. The curved portion 36 may comprise various shapes, for example, a ramp-shaped curve as shown in FIG. 1 and FIG. 3, or alternatively, a longitudinally-oriented dome-shaped recess 136 as shown in FIG. 4, or a radially-oriented dome-shaped recess 236 as shown in FIG. 5. Other curved shapes may be employed. Moreover, multiple curved portions may be employed, for example, as explained below with respect to FIG. 5.

While the recessed portion is generally described below as comprising one or more curved portion 36, 136 or 236, the recessed portion alternatively may comprise other shapes. For example, the recessed portion 36 may comprise a short, straight tapered section of core member 22. In accordance with one aspect, the recessed portion 36 spans a relatively short longitudinal length with respect to the taper 26, as shown in FIG. 1.

In accordance with one aspect, the proximal end 42 of the first coiled member 40 is at least partially seated within the curved portion 36 of the core member 22. The provision of the curved portion 36 at the junction between the main body 24 and the taper 26 allows the proximal end 42 of the first coiled member 40 to rest adjacent to the core member 22 such that it forms a substantially flush exterior surface with the core member 22, as shown in FIG. 1 and FIG. 3.

In accordance with another aspect, the proximal end 42 of the first coiled member 40 comprises adjacent turns that are spaced apart further relative to adjacent turns disposed near a central region of the first coiled member 40. As shown in FIG. 1, gaps 43 preferably are provided along the proximal end 42 in spaces between adjacent coil turns. The gaps 43 preferably are larger than other gaps that may form along a central portion and/or distal portion of the first coiled member 40, as depicted in FIG. 1. Advantageously, the increased spacing of the gaps 43 permits the solder 67 to flow between the gaps in order to adhere the proximal end 42 of the first coiled member 40 to the core member 22.

The gaps 43 may be integrally formed with the first coiled member 40, i.e., the coil itself may be produced with the spacing pattern shown in FIG. 1. Alternatively, the gaps 43 may be formed when the first coiled member 40 is attached to the core member 22, e.g., by applying a tensile force to the central region or the distal end 44 of the first coiled member 40, while holding the proximal end 42 steady with respect to the distal end 44 and the core member 22. The tensile force may be applied manually or using mechanical means. While under tension, the proximal end 42 may be soldered to the core member 22, preferably along the taper 26, as shown in FIG. 2. Once the adhering step of proximal end 42 is complete, the tensile force may be removed, and the central and distal regions of the first coiled member 40 may return to their relaxed states in which adjacent turns are closer to one another.

The provision of the gaps 43, in conjunction with the provision of the curved portion 36, allows the proximal end 42 of the first coiled member 40 to be soldered to the core member 22 without substantially increasing the overall radial profile of the wire guide 20, as shown in FIG. 1 and FIG. 3. Specifically, the diameter of the wire guide 20 in the vicinity of the solder 67 is approximately the same as the diameter of the main body 24, as shown in FIG. 1 and FIG. 3. Advantageously, a substantially smooth and flush outer wire guide surface is provided, without significant bumps or inconsistencies. The uniformity in outer diameter and reduced profile in the region of the solder 67 may enhance navigability of the wire guide 20 and facilitate delivery into smaller vessels.

In a preferred embodiment, the wire guide 20 further comprises a second coiled member 50 having proximal and distal ends 52 and 54, respectively. The second coiled member 50 is disposed distal to the first coiled member 40, as shown in FIG. 1. Preferably, the distal end 44 of the first coiled member 40 is at least partially intertwined with the proximal end 52 of the second coiled member 50, as shown in FIG. 1. Intertwining may be achieved by placing at least one turn of the first coiled member 40 adjacent to at least one turn of the second coiled member 50. Preferably, at least three turns at the distal end 44 of the first coiled member 40 are disposed adjacent to at least three turns at the proximal end 52 of the second coiled member 50, as shown in FIG. 1.

The intertwining of portions of the first coiled member 40 and the second coiled member 50 preferably is situated in the vicinity of the second taper 28. Alternatively, the intertwining may be disposed further proximally towards the taper 26, or further distally towards the reduced diameter section 30. Portions of the distal end 44 of the first coiled member 40 and/or the proximal end 52 of the second coiled member 50 may be attached to the core member 22 using any suitable technique, for example, soldering, welding or using a biocompatible glue.

Preferably, the cross-sectional diameter of the second coiled member 50 is greater than the cross-sectional diameter of the first coiled member 40, as depicted in FIG. 1. It should be noted that although the larger cross-sectional diameter of the second coiled member 50 is disposed substantially adjacent to the reduced diameter section 30 of the core member 22, the overall profile of wire guide 20 is not increased. More specifically, the profile is not increased because an inner surface of the second coiled member 50 may be disposed slightly inward relative to an inner surface of the first coiled member 40, as shown in FIG. 1. Accordingly, an outer diameter of the first coiled member 40 may be substantially the same as an outer diameter of the second coiled member 50.

In a presently preferred embodiment, the first coiled member 40 comprises stainless steel and the second coiled member 50 comprises palladium. Visualization of the distal region of the wire guide 20 may be enhanced due to the radiopacity of palladium. Further, since the cross-sectional diameter of the second coiled member 50 is greater than the cross-sectional diameter of the first coiled member 40, improved visualization near the distal tip may be achieved.

In the embodiment of FIG. 1, the distal end 54 of the second coiled member 50 may be attached to an atraumatic tip 70, which may comprise a rounded solder. The distal tip section 34 of the core member 22 also may be attached to the atraumatic tip 70, as shown in FIG. 1.

The wire guide 20 further preferably comprises a shaping ribbon 60, which may be positioned near the distal tip of the wire guide 20. In a preferred embodiment, the shaping ribbon 60 is disposed substantially beneath the second coiled member 50, as shown in FIG. 1.

The shaping ribbon 60 may comprise a stainless steel wire having a flat cross-sectional profile, as depicted in FIG. 2. Alternatively, other shapes and cross-sectional materials may be employed. By way of example, the shaping ribbon 60 may comprise a thickness of about 0.001 inches, a width of about 0.003 inches, and a longitudinal length of about 1.1 inches.

A distal end of the shaping ribbon 60 may be attached to the atraumatic tip 70, as shown in FIG. 1. A proximal end of the shaping ribbon 60 may be disposed near the junction where the distal end of the first coiled member 40 is intertwined with the proximal end of the second coiled member 50, as shown in FIG. 1. Solder may be used to fuse the shaping ribbon 60 to the first coiled member 40, the second coiled member 50, and/or the core member 22.

In use, the shaping ribbon 60 may be bent prior to insertion of the wire guide 20 in order to achieve a desired curvature at the distal tip of the wire guide 20. In this manner, a physician may tailor the wire guide to have a preferred curvature suitable for use in a particular application or vessel. It should be noted that the shaping ribbon 60 preferably is configured such that the distal tip of wire guide 20 retains a sufficiently high degree of flexibility to allow the wire guide to navigate tortuous vasculature.

Wire guide 20 may be coated with any suitable substance for facilitating insertion and/or navigability through a patient's vasculature. For example, when the core member 22 comprises nitinol, it may be coated with parylene to provide electrical insulation, thereby allowing electrosurgical devices to be used with the wire guide 20. A coating of parylene having a thickness on the level of microns may provide enhanced electrical insulation for the wire guide 20, as compared to a Teflon coating on the level of millimeters. A wire guide having a combined linear elastic nitinol with a parylene coating therefore is preferred in order to provide a thinner wire guide having increased pushability and electrical resistance, while maintaining flexibility and kink resistance. Still other coatings may be applied to wire guide 20 to provide additional lubricity, if desired.

Referring now to FIG. 4, an alternative wire guide 120 is similar to the wire guide 20 of FIGS. 1-3, with variations shown near the distal end of the main body 24 of the core member 22, as explained further below. In particular, a curved portion 136 of the wire guide 120 comprises a longitudinally-oriented dome-shaped recess 136, as shown in FIG. 4. The curved portion 136 may be disposed around the entire circumference of the wire guide 120, preferably near the junction between the main body 24 and the taper 26. The proximal end 42 of the first coiled member 40 may be at least partially seated within the curved portion 136 of the wire guide 120, thereby forming a substantially flush exterior surface with the core member 22, as shown in FIG. 4.

Referring now to FIG. 4, an alternative wire guide 120 is similar to the wire guide 20 of FIGS. 1-3, with variations shown near the distal end of the main body 24 of the core member 22, as explained further below. In particular, a curved portion 136 of the wire guide 120 comprises a proximal apex 137, an outer shoulder 138, and an inner shoulder 139, as shown in FIG. 4. In one embodiment, the curved portion 136 comprises a concave shape in which the proximal apex 137 is disposed between the outer and inner shoulders 138 and 139. In this example, the outer and inner shoulders 138 and 139 are each positioned distally of the proximal apex 137, as shown in FIG. 4. In one non-limiting example, the distance between the outer and inner shoulders 138 and 139 may be about 180 degrees, in which case the proximal apex may be about 90 degrees from each of the outer and inner shoulders 138 and 139. In one embodiment, the outer shoulder 138 is positioned approximately directly radially outward relative to the inner shoulder 139. In other examples, the distance between the outer and inner shoulders 138 and 139 may be greater than 180 degrees. In various embodiments, the curved portion 136 may be disposed around the entire circumference of the wire guide 120, preferably near the junction between the main body 24 and the taper 26. The proximal end 42 of the first coiled member 40 may be at least partially seated within the curved portion 136 of the wire guide 120, thereby forming a substantially flush exterior surface with the core member 22, as shown in FIG. 4.

Referring now to FIG. 5, an alternative wire guide 220 is similar to wire guide 20 of FIGS. 1-3, with main exceptions noted below. In particular, multiple curved portions 236 are provided. Moreover, the curved portions 236 comprise generally radially-oriented dome-shaped recesses 236, as shown in FIG. 5. In this embodiment, the main body 24 transitions to a reduced diameter region 257 via a step 255, and the multiple curved portions 236 are formed in lateral surfaces of the reduced diameter region 257, as shown in FIG. 5. The curved portions 236 may be disposed around the entire circumference of the core member 22, or alternatively may be formed as dimple-shaped protrusions in the core member 22 at selected locations along the reduced diameter region 257.

The proximal end 42 of the first coiled member 40 may be at least partially seated within the curved portions 236 of the wire guide 220, thereby forming a substantially flush exterior surface with the main body 24, as shown in FIG. 5. Further, as noted above, the proximal end 42 of the first coiled member 40 preferably comprises adjacent turns that are spaced apart further relative to adjacent turns disposed near a central or distal region of the first coiled member 40. The provision of the gaps 43, in conjunction with the provision of the curved portions 236 and the reduced diameter region 257, allows the proximal end 42 of the first coiled member 40 to be soldered to the core member 22 without substantially increasing the overall radial profile of the wire guide 220. Specifically, the diameter in the vicinity of the solder 67 is approximately the same as the diameter of the main body 24, as shown in FIG. 5.

In use, wire guides 20, 120 and 220 may be particularly suitable for delivery into peripheral vessels, but also may be used to navigate other vasculature, such as coronary vessels. The features discussed above allow wire guides 20, 120 and 220 to be flexible enough to navigate tortuous vasculature, but also rigid enough to permit the introduction of medical components, such as a catheter, over the wire guides.

While various embodiments of the invention have been described, it will be apparent to those of ordinary skill in the art that many more embodiments and implementations are possible within the scope of the invention. Accordingly, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A wire guide suitable for use in a body vessel, the wire guide comprising:
    a core member having proximal and distal ends and at least one recessed portion disposed therebetween, wherein the recessed portion comprises a concave shape in which a proximal apex is disposed between outer and inner shoulders;
    a first coiled member having proximal and distal ends, wherein the proximal end of the first coiled member is seated at least partially within the recessed portion of the core member, thereby forming a substantially flush exterior surface with the core member; and
    at least one taper disposed distal to the recessed portion of the core member, wherein the taper reduces the diameter of the core member at a location distal to the recessed portion.

2. The wire guide of claim 1 wherein the recessed portion spans a longitudinal length that is significantly shorter than a longitudinal length spanned by the taper.

3. The wire guide of claim 1 wherein a distance between the outer and inner shoulders spans a length of greater than 180 degrees.

4. The wire guide of claim 1 wherein the first coiled member comprises a first set of adjacent turns disposed at an attachment region to the core member, the attachment region disposed at the proximal end of the first coiled member, wherein the first set of adjacent turns comprise a first spacing relative to one another,
    wherein the first coiled member further comprises a second set of adjacent turns disposed at a non-attachment region distal to the first set of adjacent turns, wherein the second set of adjacent turns comprise a second spacing relative to one another,
    wherein the first spacing is greater than the second spacing.

5. The wire guide of claim 4 wherein the first coiled member is soldered to the core member in the vicinity of the recessed portion, wherein solder is disposed substantially within the first set of adjacent turns, such that the solder does not significantly increase the overall profile of the wire guide.

6. The wire guide of claim 1 further comprising a second coiled member having proximal and distal ends, wherein the second coiled member is disposed distal to the first coiled member, and wherein the distal end of the first coiled member is at least partially intertwined with the proximal end of the second coiled member.

7. The wire guide of claim 6 wherein the cross-sectional diameter of the second coiled member is greater than the cross-sectional diameter of the first coiled member.

8. The wire guide of claim 7 wherein an inner surface of the second coiled member is disposed inward relative to an inner surface of the first coiled member, such that an outer diameter of the first coiled member is substantially the same as an outer diameter of the second coiled member.

9. The wire guide of claim 6 further comprising a shaping ribbon disposed adjacent to the distal end of the core member and further disposed substantially beneath the second coiled member.

10. The wire guide of claim 1 wherein the core member comprises a linear elastic nickel titanium alloy.

11. The wire guide of claim 10 further comprising a parylene coating disposed over at least a portion of an outer surface of the core member.

12. The wire guide of claim 1 where the outer and inner shoulders are each positioned distally of the proximal apex.

13. The wire guide of claim 1 where the distance between the outer and inner shoulders is about 180 degrees, such that the proximal apex is positioned about 90 degrees from each of the outer and inner shoulders.

14. The wire guide of claim 1 where the outer shoulder is positioned approximately directly radially outward relative to the inner shoulder.

15. A method for manufacturing a wire guide, the method comprising:
    providing a core member having proximal and distal ends and at least one recessed portion disposed therebetween;
    providing a first coiled member having proximal and distal ends, wherein the proximal end of the first coiled member is seated at least partially within the recessed portion of the core member, thereby forming a substantially flush exterior surface with the core member;
    providing a first set of adjacent turns of the first coiled member disposed at an attachment region to the core member, the attachment region disposed at the proximal end of the first coiled member, wherein the first set of adjacent turns comprise a first spacing relative to one another,
    providing a second set of adjacent turns disposed at a non-attachment region distal to the first set of adjacent turns, wherein the second set of adjacent turns comprise a second spacing relative to one another,
    wherein the first spacing is greater than the second spacing;
    soldering the first coiled member to the core member in the vicinity of the recessed portion, wherein solder is disposed substantially within the first set of adjacent turns, such that the solder does not significantly increase the overall profile of the wire guide, and
    holding the proximal end of the first coiled member substantially steady;
    applying a tensile force to a portion of the first coiled member to provide gaps between adjacent coil turns along the attachment region;
    applying solder between the first set of adjacent turns at the attachment region to adhere the first coiled member to the core member; and
    removing the tensile force.

16. The method of claim 15 further comprising:
    providing a second coiled member having proximal and distal ends, wherein the second coiled member is disposed distal to the first coiled member; and
    intertwining at least a portion of the distal end of the first coiled member with at least a portion of the proximal end of the second coiled member.

17. A wire guide suitable for use in a body vessel, the wire guide comprising:
    a core member having proximal and distal ends and at least one recessed portion disposed therebetween, wherein the recessed portion comprises a concave shape in which a proximal apex is disposed between outer and inner shoulders; and
    a first coiled member having proximal and distal ends, wherein the proximal end of the first coiled member is seated at least partially within the recessed portion of the core member, thereby forming a substantially flush exterior surface with the core member,
    wherein the first coiled member comprises a first set of adjacent turns disposed at an attachment region to the core member, the attachment region disposed at the proximal end of the first coiled member, wherein the first set of adjacent turns comprise a first spacing relative to one another,
    wherein the first coiled member further comprises a second set of adjacent turns disposed at a non-attachment region distal to the first set of adjacent turns, wherein the second set of adjacent turns comprise a second spacing relative to one another,
    wherein the first spacing is greater than the second spacing.

18. A wire guide suitable for use in a body vessel, the wire guide comprising:
    a core member having proximal and distal ends and at least one recessed portion disposed therebetween, wherein the recessed portion comprises a concave shape in which a proximal apex is disposed between outer and inner shoulders;
    a first coiled member having proximal and distal ends, wherein the proximal end of the first coiled member is seated at least partially within the recessed portion of the core member, thereby forming a substantially flush exterior surface with the core member; and
    a second coiled member having proximal and distal ends, wherein the second coiled member is disposed distal to the first coiled member, and wherein the distal end of the first coiled member is at least partially intertwined with the proximal end of the second coiled member.

* * * * *

UNITED STATES PATENT AND TRADEMARK OFFICE
CERTIFICATE OF CORRECTION

PATENT NO.       : 8,360,995 B2                                              Page 1 of 1
APPLICATION NO.  : 12/677973
DATED            : January 29, 2013
INVENTOR(S)      : Elsesser et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 69 days.

Signed and Sealed this
First Day of September, 2015

Michelle K. Lee
*Director of the United States Patent and Trademark Office*